United States Patent [19]

Akiyama

[11] Patent Number: 5,024,520
[45] Date of Patent: Jun. 18, 1991

[54] OPHTHALMIC MEASUREMENT APPARATUS
[75] Inventor: Koichi Akiyama, Hino, Japan
[73] Assignee: Kowa Company Ltd., Japan
[21] Appl. No.: 464,903
[22] Filed: Jan. 16, 1990
[30] Foreign Application Priority Data
   Jan. 23, 1989 [JP] Japan .................................. 1-12015
[51] Int. Cl.⁵ ................................................ A61B 3/10
[52] U.S. Cl. .................................... 351/221; 351/206; 351/214
[58] Field of Search ......................... 351/214, 221, 206
[56] References Cited
   U.S. PATENT DOCUMENTS
   4,711,542 12/1987 Ichihashi et al. ................... 351/221
   4,877,321 10/1989 Ichihashi et al. ................... 351/214

Primary Examiner—Paul M. Dzierzynski
Attorney, Agent, or Firm—Bruce L. Adams; Van C. Wilks

[57] ABSTRACT

An ophthalmic measurement apparatus in which the interior of a patient's eye is irradiated with a laser beam and the light scattered from the eye is detected and processed to determine the protein concentration in the eye. The apparatus employs a single-objective binocular observation section and a total-reflection mirror which allow these measurements to be carried out without decreasing the amount of light impinging on the photodetector used to detect the scattered light or the amount of light used by an observation section, and the apparatus can also be used as a slit-lamp microscope.

8 Claims, 6 Drawing Sheets

OPHTHALMIC MEASUREMENT APPARATUS

BACKGROUND OF THE INVENTION

1. Field of the Invention

This invention relates to an ophthalmic measurement apparatus, and more particularly to an ophthalmic measurement apparatus in which a laser beam is projected at a selected spot in an eye under examination and laser light scattered therefrom is detected for ophthalmic measurement.

2. Description of the Prior Art

Measurement of protein concentration (the flare components) in the aqueous chamber of the anterior camera oculi is of considerable importance in determining whether the camera oculi is inflamed, that is, whether the blood-aqueous barrier function is normal or not. A number of methods are employed for carrying out this measurement. One method frequently used employs a slit lamp microscope to grade the concentration by naked-eye observation, while a photographic measuring method has been developed as a way of measuring the protein concentration quantitatively. In another method, a beam of laser light is directed into the eye and the light scattered from the eye is detected and quantitatively analyzed. With the method employing laser light, a laser beam from a laser light source in a projection section is converged at a selected spot in the camera oculi of the eye together with a slit image, thereby providing illumination around the spot so that, via an observation section, the projected laser beam and slit image can be observed. To carry out the ophthalmic measurement, the scattered light from the eye is detected by a photodetector which converts the light into electrical signals that are then processed.

In this type of ophthalmic measurement apparatus, a beam splitter or semi-transparent mirror is used to divide the scattered light from the eye into light that is guided to the photodetector and light that is guided to the observation section (see Japanese Patent Publication 63-55928 and Japanese Laid-open Patent Application 63-315030 corresponding to U.S. patent application Ser. No. 206,518 filed on June 14, 1988). As the beam splitter or semi-transparent mirror usually reduces the amount of light by half, the amount of light available for observation purposes also is reduced. If I1 is the amount of incident light reaching the observation section, I2 is the amount of incident light at the photodetector and the transmittance of the beam splitter or semi-transparent mirror is 50%, then $I1 = I2 = \frac{1}{2}$, thus I1 is half the amount it would be if there were no beam splitter or semi-transparent mirror. This is a major drawback when a slit lamp microscope is used. One solution is to use a lens with a large aperture, but the resulting increase in the cost and size of the apparatus makes this impractical. On the other hand, the increase in the amount of light to the observation section decreases the amount of incident light at the photodetector, thus impeding the measurement of flare components.

In Japanese Laid-open Patent Application 63-315030, an arrangement is used in which P-polarized light impinges on a semi-transparent mirror, but the efficiency of this is low. To improve the efficiency, a $\lambda/2$ plate is provided in front of the semi-transparent mirror and the plane of polarization is rotated 90 degrees so that S-polarized light impinges on the semi-transparent mirror, increasing the amount of light received by the light receiving section. By changing the scattered light impinging on the semi-transparent mirror into S-polarized light, the amount of light impinging on the photodetector can be increased without affecting the amount of light received by the observation section. However, a $\lambda/2$ plate is expensive and raises the overall cost of the apparatus, while another disadvantage is that the apparatus cannot be used as a slit lamp microscope.

SUMMARY OF THE INVENTION

An object of the present invention is therefore to provide an ophthalmic measurement apparatus which allows measurements to be carried out without a decrease either in the amount of light received by the photodetector or in the amount of light received by the observation section.

To attain the above object, the observation section for observing the laser beam in the eye and the projected slit image is configured as a single-objective binocular system, and a total-reflection mirror is used to divide the scattered light from the eye into light that is guided to the photodetector and light that is guided to the observation section. With this arrangement, scattered laser light can be directed to the observation section via apertures provided in the total-reflection mirror to thereby provide an ophthalmic measurement apparatus which allows measurements to be carried out without a decrease either in the amount of light received by the photodetector or in the amount of light received by the observation section. Thus, the apparatus can readily be utilized as a slit-lamp microscope.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

The invention will now be described in detail on the basis of the preferred embodiments illustrated in the drawings.

Figure 1:
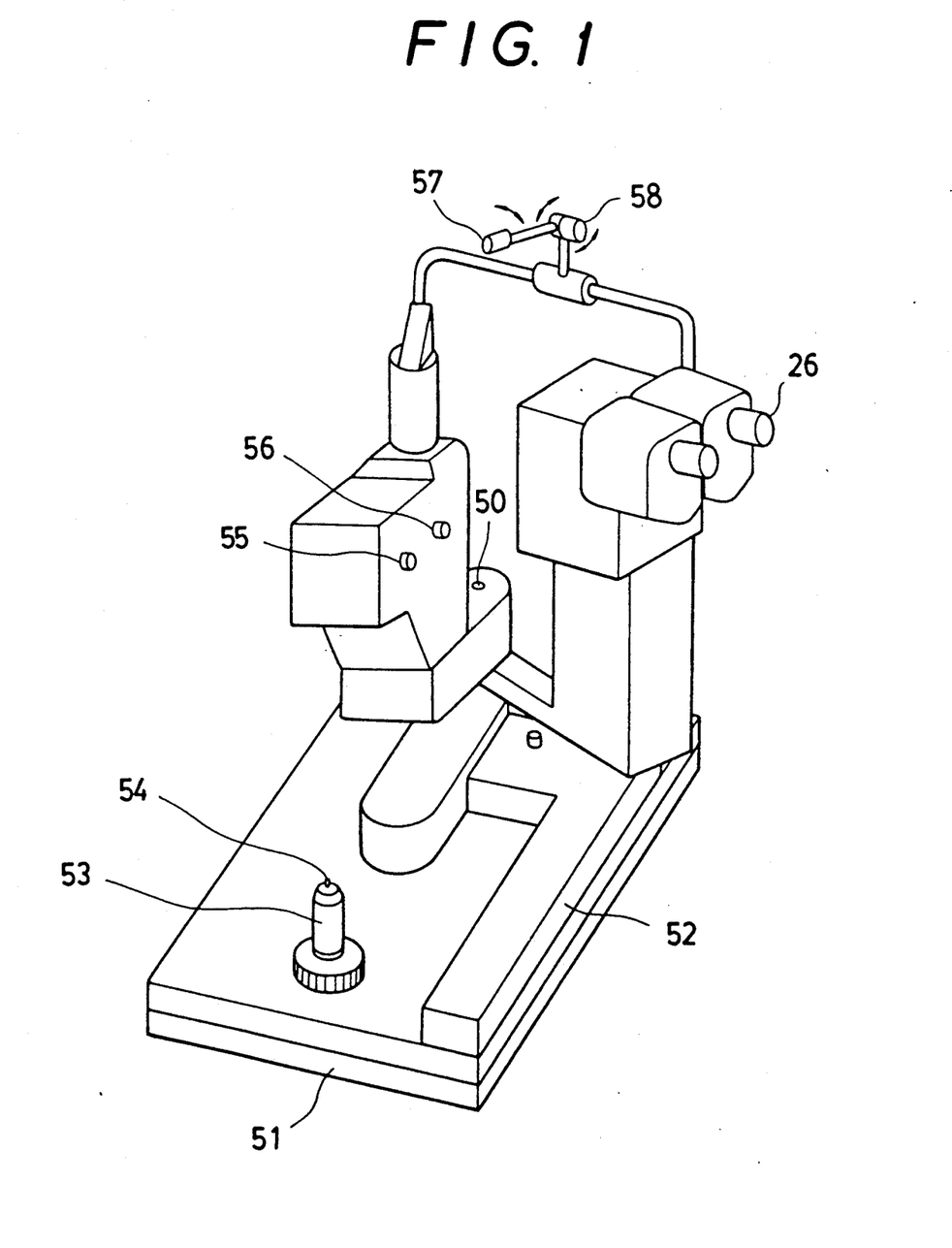
FIG. 1 is a perspective view showing the structural arrangement of the ophthalmic measurement apparatus of the present invention.
Figure 2:
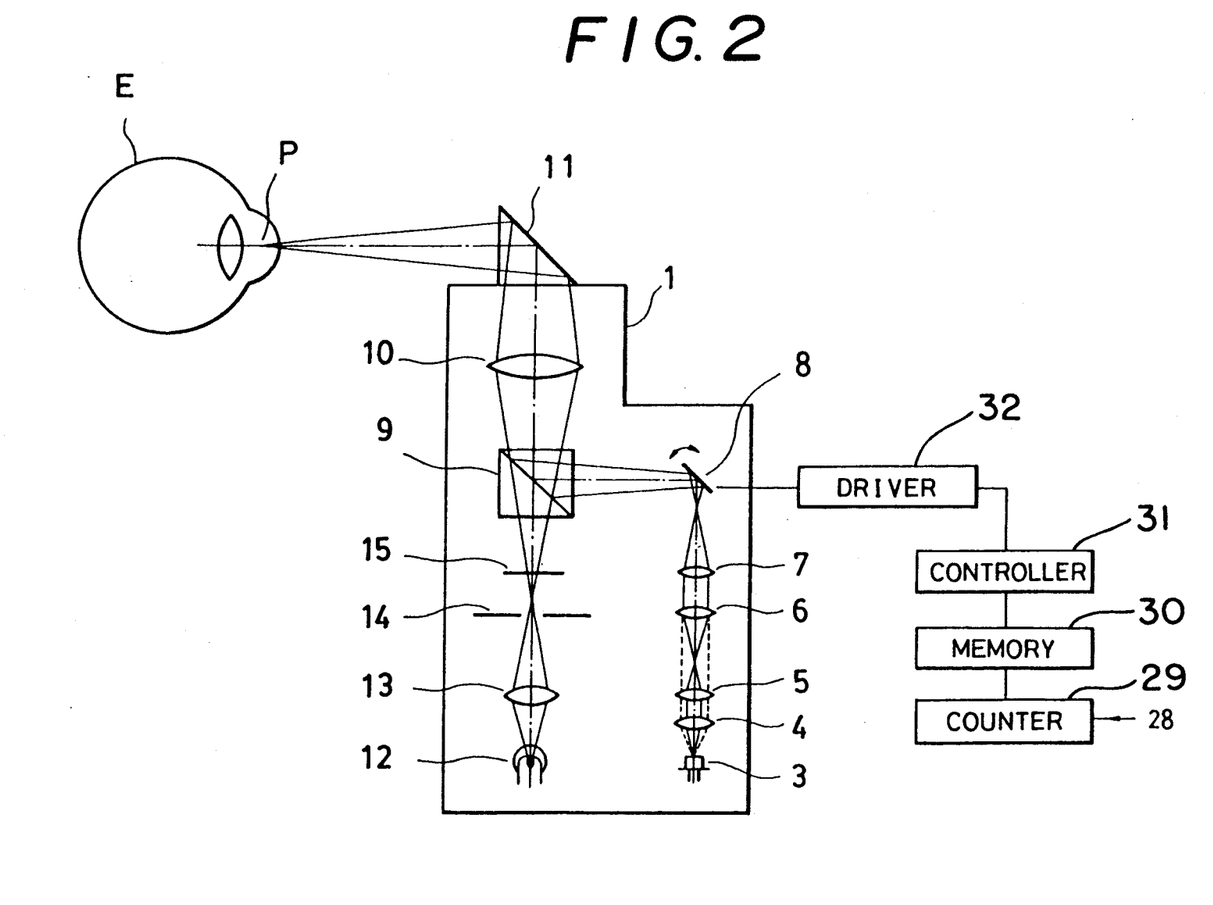
FIG. 2 is a side view showing the internal configuration of the projection section of the apparatus shown in FIG. 1.
Figure 3:
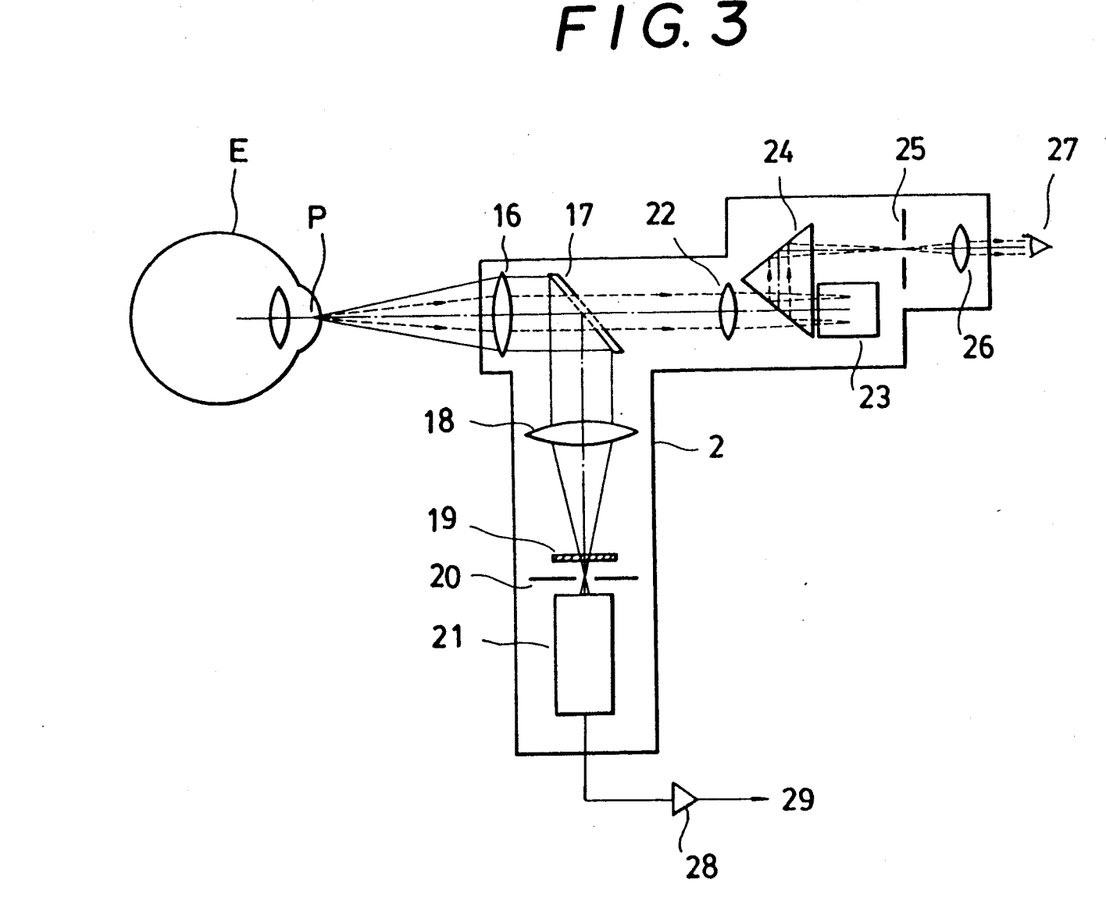
FIG. 3 is a side view showing the internal configuration of the configuration of the light receiving section.

FIGS. 1 to 3 show the general configuration of the embodiment of the ophthalmic measurement apparatus of this invention. In the drawings, reference numeral 1 denotes a laser light projection section in which a semiconductor laser or other such laser light source 3 is disposed. The laser beam from the laser light source 3 is formed into an elliptical parallel beam by a collimating lens 4 and is then formed into a round parallel beam by a beam expander constituted by lenses 5 and 6. After passing through a relay lens 7, an optical scanner 8, a beam-splitter 9, a lens 10 and a prism 11, the beam is converged on a predetermined point P in the anterior chamber of the eye under examination E.

The optical scanner 8 is connected to a drive circuit 32 controlled by a control section 31 constituted by a microprocessor or the like. This arrangement allows the deflecting angle of the optical scanner 8 to be adjusted. The laser beam can thus be deflected about a center formed by the point of convergence P by adjusting the angle of the optical scanner 8.

The laser light projection section 1 is provided with a light source 12, such as a halogen lamp, for illuminating the slit. White light from the light source 12 illuminates a slit 14 via a lens 13. The light from the slit 14 thus illuminated passes via a shutter 15, the beam splitter 9, the lens 10 and the prism 11 to form a slit image in the vicinity of the point of convergence P in the anterior chamber of the eye. By illuminating the area around the point of convergence P, the slit image allows the position of the point of convergence P to be readily confirmed when measuring the protein concentration in the anterior chamber.

The width and length of the slit 14 can be adjusted by a slit width adjustment knob 56 and slit length adjustment knob 55 to enable the apparatus to be utilized also as a slit-lamp microscope.

The shutter 15 can be closed when the protein concentration is being measured. The shutter 15 is inserted into, or retracted from, the corresponding optical system by operating an input device such as a joystick 53 equipped with a push-button switch 54.

A light receiving section 2, shown in FIG. 3, is for receiving scattered light from the vicinity of the point of convergence P and for allowing observation of the region. For this, scattered light from the point of convergence P in the anterior chamber of the eye under examination E passes through a lens 16, is reflected by a total-reflection mirror 17 provided with apertures (FIG. 4) and passes, via a lens 18, interference filter 19 and mask 20 to a photomultiplier 21 which constitutes the photodetector. The interference filter 19 is a narrow-band interference filter with a peak wavelength corresponding to the wavelength of the light of the laser light projection section 1 and blocks external light, to enable it to be used in a half darkroom. The field of view is defined by a mask 20 which prevents light outside the region of interest from impinging on the photomultiplier 21, for which the mask 20 is provided at a position that is conjugate with the point of convergence P.

Use of an interference filter eliminates the need to provide a shutter in front of the photomultiplier. If, however, a shutter is provided to be on the safe side, as in the case of shutter 15, the shutter is inserted into, or retracted from, the corresponding optical system by operating an input device such as a joystick 53.

The output from the photomultiplier 21 is passed through an amplifier 28 and input to a counter 29 which counts the intensity of the scattered light detected by the photomultiplier as a pulse count per unit time period. The output of the counter 29, i.e., the number of samplings or the total pulse count for each unit time period, is stored in a specific memory cell of a memory 30. The data thus stored in the memory 30 is arithmetically processed by the control section 31 to compute the protein concentration in the anterior chamber.

Provided to the rear of the total-reflection mirror 17 of the light receiving section is an observation section for observing a region in the eye centering on the point of convergence. Specifically, light that passes through the apertures 17b of the total-reflection mirror 17 can be observed by an examiner 27 via a lens 22, erect prisms 23 and 24, field stop 25 and eyepiece 26. This observation section enables the projected laser beam and harmful light rays to be observed while the measurement of the protein concentration is being carried out; when the apparatus is used as a slit-lamp microscope, the eyeball is viewed in cross-section.

In this embodiment, an eye fixation light 57 constituted by a light-emitting diode, for example, is provided at a position that permits the examiner to fix the patient's eye. The eye fixation light 57 can be turned in the direction indicated by the arrow by means of a link mechanism 58 to enable it to be adjusted to the best position with respect to the patient undergoing the eye examination. The light selected for the eye fixation light 57 is of a different color than the laser light.

Provided on a base 51 is an input means such as the joystick 53 equipped with the push-button 54, the operation of which, as described above, causes optical elements such as the shutter 15 to be inserted into, or retracted from, the optical system concerned.

Figure 5:
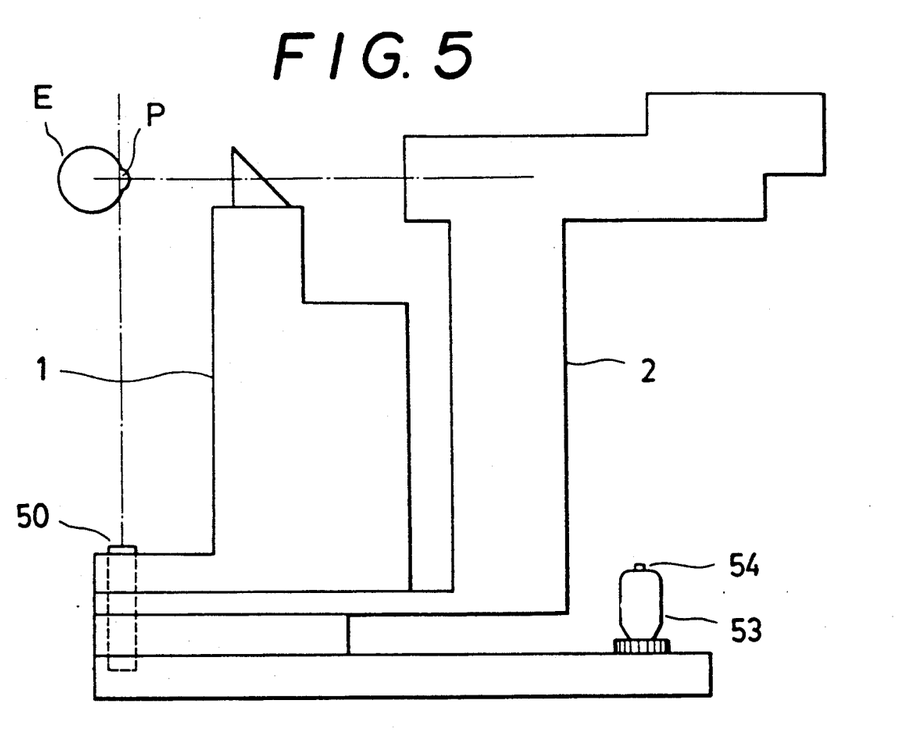
FIG. 5 is a side view showing the apparatus in FIG. 1.
Figure 6:
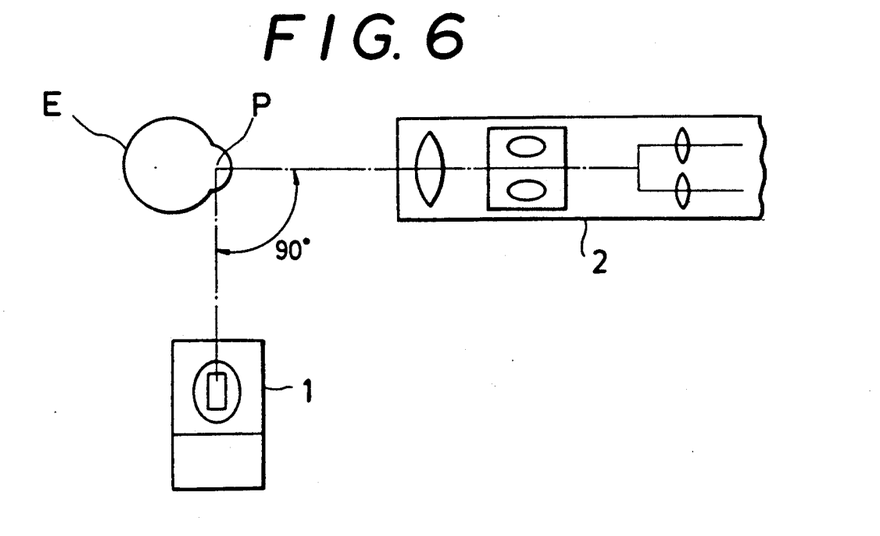
FIG. 6 is a plan view showing the apparatus in FIG. 1.

As shown in FIG. 5, the laser light projection section 1 and light receiving section 2 can be rotated independently in a horizontal plane about a shaft 50. When measuring the anterior chamber protein concentration the laser light projection section 1 and the light receiving section 2 are set at an angle of 90 degrees, as shown in FIG. 6. When the apparatus is to be used as a slit-lamp microscope the sections are unlocked to allow them to be rotated freely for observation of the eye in cross-section. When used thus, the point of convergence P is arranged so as to be positioned directly over the shaft 50.

A power source circuitry box 52 contains various components and circuitry including the control section 31, memory 30, counter 29 and power supply.

The overall measurement procedure will now be described. The patient's head is positioned using a conventional chin rest (not illustrated), the light source 12 is switched on to cause an image of the slit 14 to be projected onto the eye under examination E, and the laser beam from the laser light projection section 1 is converged to the point of convergence P in the eye.

Using the observation section to observe the laser beam projected into the eye together with the slit image, the apparatus is brought into alignment with the eye. When alignment and other preparatory procedures have been completed, the shutter 15 is closed and the scattered laser light is measured by the light received section 2 to determine the protein concentration in the anterior chamber of the eye. More specifically, the measurement process comprises projecting the laser beam from the laser light projection section 1 at the point of convergence P in the eye, and using the light receiving section 2 to detect scattered light from around the point of convergence P. The output from the photomultiplier 21 is passed through an amplifier 28 and input to a counter 29 which counts the intensity of the scattered light detected by the photomultiplier as a pulse count per unit time period. The output of the counter 29, that is, the number of samplings or the total pulse count for each unit time period, is stored in a specific memory cell of the memory 30. The data thus stored in the memory 30 is arithmetically processed by the control section 31 to compute the protein concentration in the anterior chamber. As this is a known measurement procedure, no further details will be described here.

Figure 4:
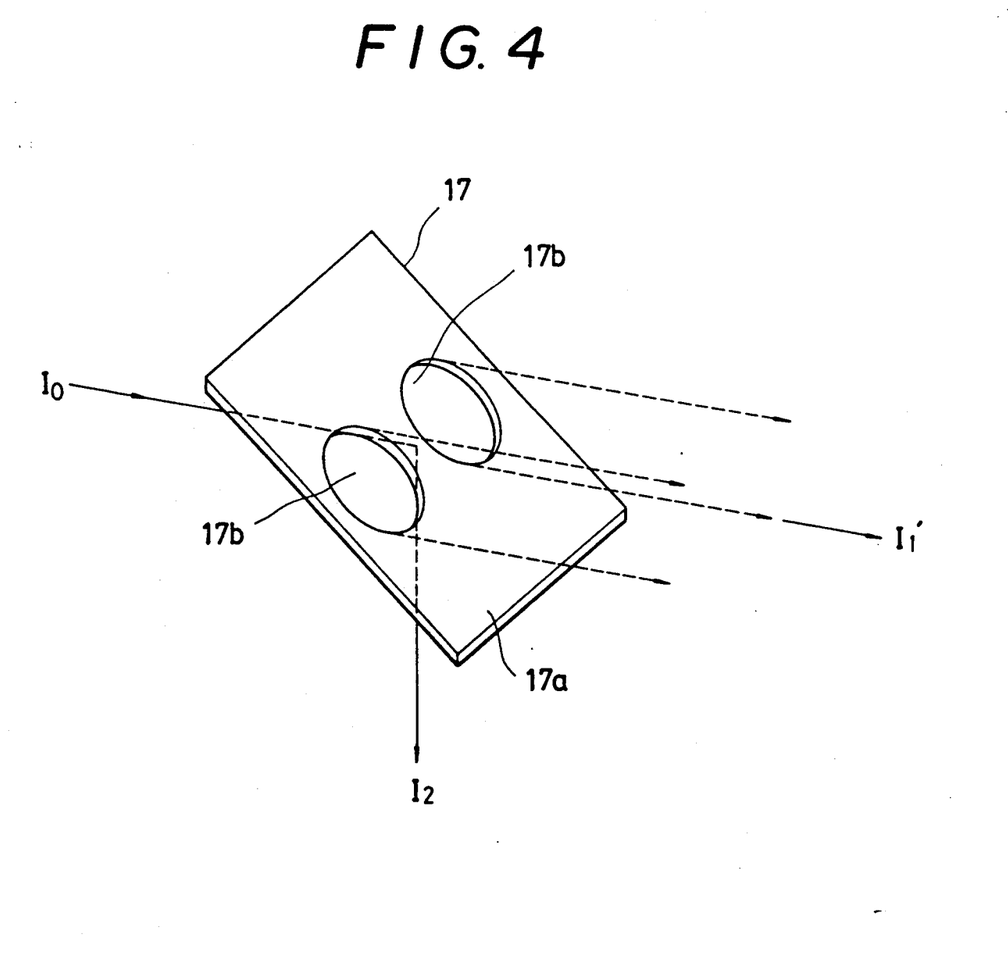
FIG. 4 is a perspective view showing the total-reflection mirror with the apertures.
Figure 7:
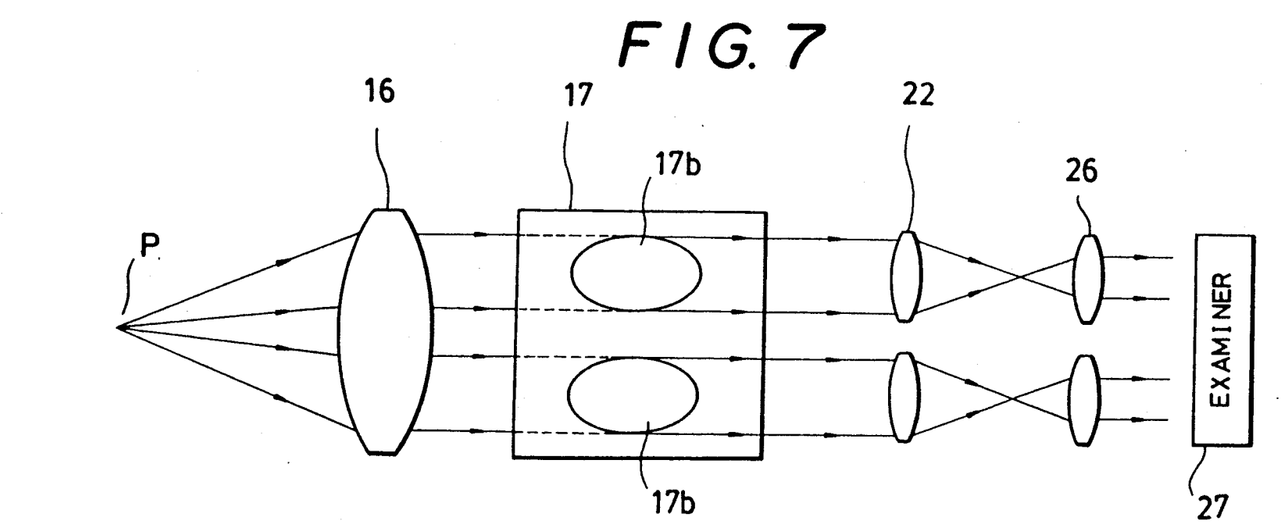
FIG. 7 is an explanatory view showing the amount of light going to the observation section.

As in this embodiment the observation section is configured as a single-objective binocular system as shown in FIGS. 4 and 7 (the erect prisms are not shown in FIG. 7), apertures 17b can be provided in the total-reflection mirror 17. The apertures 17b are large enough fully to encompass the aperture of the image formation lens 22.

By providing apertures 17b in the total-reflection mirror 17 used to split the optical path of the scattered light from the eye into one light path that goes to the photodetector and another light path that goes to the observation section, the amount of light I1' going to the observation section is not decreased by the interposition of the total-reflection mirror. The amount of light I2 that reaches the photomultiplier is determined by the effective area 17a of the total-reflection mirror 17.

If the ratio of the mirror's effective area 17a to the area of the mirror apertures is 1:1, then I2=Io/2 and I'1=2×I1, so I'1 can be made twice as large as I1 without changing I2. This hold particularly for the single-objective binocular system.

Figure 8A:
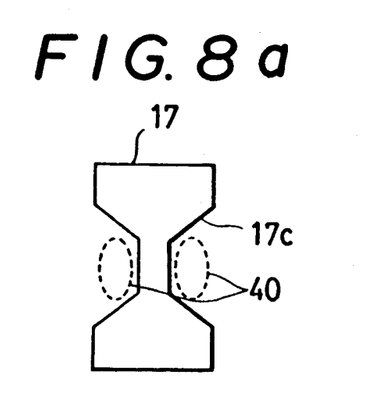
FIGS. 8a and 8b show other embodiments of the total-reflection mirror.
Figure 8B:
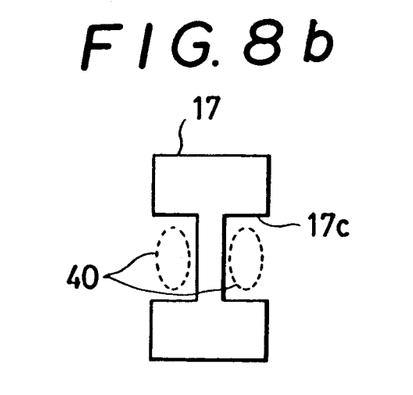

Instead of providing apertures in the total-reflection mirror 17, the type of arrangement shown in FIG. 8 may be used in which inset portions 17c are formed in the mirror 17 that are of a sufficient size to encompass observation apertures 40. However, this arrangement will produce a slight decrease in the amount of light falling on the photomultiplier 21. Provided this decrease is not a problem, it is enough to ensure that the observation apertures are not eclipsed and to use a total-reflection mirror for the other portions.

As use of a total-reflection mirror eliminates the considerations whether it should be S-polarized light or P-polarized light described in Japanese Laid-open Patent Application 63-315030, the photomultiplier can be provided in a direction in which a P-polarization appears when a semi-transparent mirror or beam splitter is used.

Thus, as the arrangement according to the present invention provides an increased amount of incident light at the observation section, the apparatus can also be employed as a slit-lamp microscope. When the apparatus is used as a slit-lamp microscope, the eyeball is viewed in cross-section. As the laser light is not required when the apparatus is used as a slit-lamp microscope, the laser light source is switched off at such times to extend its working life. However, as a helium-neon laser light source requires time to stabilize after being reactivated, when such a source is used it is preferable to use a shutter or like means to block the laser beam rather than deactivate it.

Using a semiconductor laser light source in the above embodiment enables each part of the apparatus to be made lighter and smaller. Moreover, using a total-reflection mirror to split the optical path of the scattered light from the eye into one light path that goes to the photodetector and another light path that goes to the observation section eliminates the need for considerations relating to S-polarized light and P-polarized light and therefore increases the degree of freedom of choice with respect to positioning of the photomultiplier. In turn, this enables the functions of ophthalmic measurement and slit-lamp microscope to be combined in the one apparatus.

Some of the specific advantages of using a semiconductor laser light source will now be described, as follows.

(a) Because a semiconductor light source is light and compact, optical axis alignment is easier. The apparatus can be made lighter, smaller and cheaper, and there is a greater range of freedom as to where the light source is provided in the apparatus, thereby increasing the overall configurability of the optical system. In the case of the embodiment described above, it enables the laser light projection section and light receiving section to be rotated freely around the shaft 50.

(b) Various arrangements are available for controlling the injection current used to drive semiconductor lasers. A certain minimum injection current is required to start the lasing action, but usually a larger injection current is used to maintain a stable lasing action. One of the major advantages of the semiconductor laser over conventional gas lasers is that, as the laser output is proportional to the injection current, variations in the power level of the incident laser beam on the eye caused by variations in temperature or changes over time, for example, can be readily compensated for by adjusting the injection current.

(c) As the light from the semiconductor laser is linearly polarized, the power of the laser beam can be adjusting by the rotation of a polarizer inserted in the optical illumination system. Furthermore, because a semiconductor laser is so light, small and compact, the same object may be achieved by rotating the laser device itself.

(d) the range of options that are available with respect to the means of adjusting the laser power, as described in (b) and (c) above, allowing the choice of means to be tailored to the conditions and objective concerned, and the ability to combine such means when necessary, are major advantages that hitherto have not been available.

Compensating for variations in the power level of the laser beam is of critical importance in view of the extremely low intensities of the light that has to be detected in the case of lasers for ophthalmic applications. A disadvantage of diverting part of the detected light for monitoring purposes and using the light amount data thus acquired for software-based compensation is that it requires an optical system for the monitoring. As a semiconductor laser incorporates an optical system for monitoring purposes, the light amount can be adjusted directly merely by adjusting the injection current that drives the light source, which is highly advantageous in terms of simplicity and reliability.

Owing to the extremely low intensity of the scattered light that has to be measured, conventional systems are highly susceptible to power variations in the laser beam projector and part of the detected light has to be diverted for monitoring purposes and software used to compensate the measurement results obtained on the basis of the light amounts thus acquired. As the above-described embodiment of the present invention, however, uses a semiconductor laser light source, the light amount can be modulated directly and the projector output maintained at a constant level by electrical means alone, which simplifies the apparatus and reduces its cost.

Moreover, the ability of the laser light projection section and the light receiving section to be rotated independently of each other ensures that the apparatus can also be used as a slit-lamp microscope.

As has been described in the foregoing, in this invention the observation section for observing the laser beam in the eye and the projected slit image is configured as a single-objective binocular system, and a total-reflection mirror is used to divide the scattered light from the eye into light that is guided to the photodetector and light that is guided to the observation section, an arrangement that enables scattered laser light to be used by the observation section without decreasing the amount of light impinging on the photodetector. Also, it provides more options as to where the photomultiplier is positioned. Thus, this provides a system that combines to a high degree the functions of a flare component measurement apparatus and of a slit-lamp microscope.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measurement apparatus in which a laser beam is projected at a selected spot in an eye under examination and laser light scattered therefrom is detected for ophthalmic measurement, comprising:
   a laser light source for producing the laser beam;
   a laser beam projector for projecting the laser beam at the selected spot in the eye under examination;
   an optical slip projector for projecting a slit image onto the selected spot int he eye;
   a light receiving section including photodetector means for detecting the laser light scattered from the eye;
   a single-objective binocular type observation section for observing the selected spot in the eye where the laser beam and slit image are projected;
   a mirror for splitting the optical path of the scattered laser light from the eye into a light path that directs light to the photodetector means and a light path that directs light to the observation section, wherein the mirror has a pair of apertures in the light path that directs light to the observation section and the ratio of the effective area of the mirror to the area of the apertures is about 1:1;
   wherein the observation section includes a pair of lenses each configured to view substantially the same size area as each aperture; and
   processing means for processing signals received from the photodetector means to perform the ophthalmic measurement.

2. An ophthalmic measurement apparatus as set forth in claim 1, wherein the mirror is provided with means for preventing an aperture in the observation section to be eclipsed.

3. An ophthalmic measurement apparatus as set forth in claim 1, wherein the laser light projector and light receiving section are rotatable about an axis formed by the eye under examination.

4. An ophthalmic measurement apparatus as set forth in claim 1, wherein the apparatus is usable as a slit-lamp microscope.

5. An ophthalmic measurement apparatus comprising:
   means for producing a laser light beam;
   means for directing the laser light beam at a selected spot in an eye under examination;
   means for projecting a slit image onto the selected spot in the eye;
   means for detecting light scattered from the eye and for producing signals corresponding thereto;
   a mirror disposed in a light path of light scattered form the eye under examination and having a mirror surface with two apertures therein, wherein light scattered from the eye under examination passes through the two apertures in a direct light path and is reflected from the mirror surface in a reflected light path to the means for detecting light, and wherein the ratio of the effective area of the mirror surface to the area of the apertures is about 1:1;
   means for observing the selected spot in the eye under examination including two lenses each configured to view substantially the same size area as each aperture; and
   means receptive of the signals from the means for detecting light for performing an ophthalmic measurement.

6. The apparatus according to claim 5, wherein mirror has means for preventing an eclipse of the apertures.

7. The apparatus according to claim 5, further comprising means mounting the means for projecting and the means for detecting for rotation about an axis including the eye under examination.

8. The apparatus according to claim 5, wherein the apparatus is usable as a slip-lamp microscope.

* * * * *